United States Patent [19]

Decker et al.

[11] 4,410,447
[45] Oct. 18, 1983

[54] LOW-FOAMING NONIONIC SURFACTANTS

[75] Inventors: Quintin W. Decker, St. Albans; Erich Marcus, Charleston, both of W. Va.; Robert J. Morlino, Port Chester, N.Y.

[73] Assignee: Union Carbide Corporation, Danbury, Conn.

[21] Appl. No.: 206,145

[22] Filed: Nov. 12, 1980

[51] Int. Cl.³ .............................................. B01F 17/00
[52] U.S. Cl. ................................ 252/351; 252/174.21; 252/174.22
[58] Field of Search .............. 252/351, 174.21, 174.22, 252/DIG. 1, DIG. 6, 8.9; 568/625, 622; 8/137, 139

[56] References Cited

U.S. PATENT DOCUMENTS 3,770,701 11/1973 Cenker et al. .................. 252/351 X
4,340,382 7/1982 Morlino et al. ..................... 252/351

Primary Examiner—Josephine Barr
Attorney, Agent, or Firm—Jean B. Mauro

[57] ABSTRACT

A liquid low-foaming nonionic surfactant composition is provided which exhibits superior wetting characteristics and general good scouring and/or detergency properties which comprises a block-random structure represented by the formula

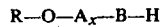

$$R-O-A_x-B-H$$

wherein R is a primary alkyl group having from 7 to 11 carbon atoms; A is oxypropylene groups; x is an integer of from 2 to 15 such that the sum of carbon atoms in R and x is from 12 to about 22, and B is a random mixture of oxyethylene and oxypropylene groups with a molar ratio of oxyethylene to oxypropylene from 1:1 to about 5:1.

6 Claims, No Drawings

LOW-FOAMING NONIONIC SURFACTANTS

BACKGROUND OF THE INVENTION

This invention relates to liquid, low-foaming nonionic surfactants, and more particularly to liquid, low-foaming nonionic surfactants having superior wetting properties and generally good scouring and detergency characteristics prepared from aliphatic alcohols having 7 to 11 carbon atoms by the sequential addition of propylene oxide and then a random mixture of ethylene oxide and propylene oxide.

Nonionic surfactants are widely used in commercial and household applications where advantage is taken of their superior performance as a wetting agent, their detergency and scouring characteristics as well as their adaptability for being combined with other types of surfactants and resistance to hard water conditions. Although nonionic surfactants as a class are generally low to moderate "foamers", they foam too much for many applications which involve vigorous agitation.

In recent years a number of nonionic surfactant products have been developed and used commercially which are designated as low-foaming or "controlled-suds" surfactants. Generally, when the need for foam suppression is of prime importance, the nonionic surfactants heretofore developed to meet this requirement have been found to have sacrificed other desirable characteristics and a need exists for materials which exhibit a wider combination of surfactant characteristics than is possible with known low-foaming nonionic products.

Surfactant properties and performance characteristics that would be desirable for many applications, in addition to foam suppression, are, for example, good scouring and/or detergency, being a liquid at room temperature, superior wetting action, and in general, low cloud points, and the development of a material which exhibited a combination and suitable balance of these factors such as superior performance in some or all of these areas while performing adequately in the others would be highly desirable.

It has long been the practice to prepare nonionic surfactants by the addition of ethylene oxide or mixtures of ethylene oxide and propylene oxide to various alcohols, which are generally long-chain monohydric alcohols. Numerous different adducts have been prepared, some of which contain only oxyethylene groups while others contain a random distribution of oxyethylene and oxypropylene groups or discrete blocks of polyoxyethylene and polyoxypropylene. For example, in U.S. Pat. Nos. 3,101,374 to Patton., 2,674,619 to Lunsted, and 2,677,700 to Jackson et al. are disclosed compositions which are prpeared by the addition of varying proportions and mixtures of alkylene oxides to reactive hydrogen compounds such as alcohols. More recent patents, such as for example, U.S. Pat. Nos. 3,770,701 to Cenker et al. and 3,956,401 to Scadera et al. disclose surfactant compositions prepared by the addition of specific proportions of ethylene oxide and propylene oxide to straight-chain aliphatic alcohols having 8 to 20 or 7 to 10 carbon atoms. The compositions disclosed in each of these patents are described as being biodegradable liquids which exhibit high detergency (U.S. Pat. No. 3,770,701) or low-foaming (U.S. Pat. No. 3,956,401) but it is not shown by either patentee that any of the compositions provide a combination of these properties or of other desirable surfactant properties such as superior wetting, nor, from the teaching thereof would one skilled in the art expect these patented compositions to exhibit such a desirable combination of properties.

SUMMARY OF THE INVENTION

In accordance with the present invention there is provided a liquid, low-foaming nonionic surfactant having superior wetting characteristics and generally good scouring and/or detergency which comprises compositions having the formula:

Wherein R is a primary alkyl group having from 7 to 11 carbon atoms: A is oxypropylene groups: x is an integer of from 2 to about 15 with the proviso that the sum of the number of carbon atoms in said alkyl group and x is at least 12: and B is a random mixture of oxyethylene groups and oxypropylene groups, the molar ratio of oxyethylene to oxypropylene in said mixture being such that the total molar ratio of oxyethylene to oxypropylene in A and B is from 0.2:1 to about 1.5:1 while the molar ratio of oxyethylene to oxypropylene in B is from 1:1 to about 5:1. Compositions of the invention have cloud points in the range from about 20° to about 60°; and preferably to about 40° C.

DESCRIPTION OF THE INVENTION

In accordance with the present invention, liquid, low-foaming nonionic surfactants having superior wetting characteristics and generally good detergent and/or scouring properties for textile materials comprise compositions obtained by reacting a primary aliphatic alcohol having from 7 to 11 carbon atoms or mixtures thereof with 2 to 15 moles of propylene oxide to form a block structure such that the sum of the number of carbon atoms in the alcohol and the number of oxypropylene groups is at least 12 and then reacting the block adduct with a random mixture of ethylene oxide and propylene oxide in a molar ratio of ethylene oxide to propylene oxide of from 1:1 to about 5:1 such that the total molar ratio of oxyethylene groups of oxypropylene groups in said surfactant is from 0.2:1 to about 1.5:1. The surfactant compositions of this invention may be represented by the following formula:

Wherein R is a primary alkyl group having from 7 to 11 and, preferably, 8 to 10 carbon atoms; A is oxypropylene groups; x is an integer of from 2 to about 15 with the proviso that the sum of the number of carbon atoms in said alkyl group and x is from 12 to about 22 and, preferably, to about 20; B is a random mixture of oxyethylene groups and oxypropylene groups, the molar ratio of oxyethylene to oxypropylene in said mixture being such that the total ratio of oxyethylene to oxypropylene in A and B is from 0.2:1 to about 1.5:1 and, preferably from 0.3:1 to 1.4:1 while the molar ratio of oxyethylene to oxypropylene in said random mixture is from 1:1, and preferably from about 2:1, to about 5:1. The R-O in the foregoing formula may also be defined as the residue of the alcohol employed in the condensation reaction, i.e., the alcohol with the hydrogen in the OH radical removed. If a mixture of alcohols is employed in the condensation reaction, the product obtained will be a mixture of compounds having the foregoing formula, the compounds differing from each other in the number of carbon atoms in the alkyl group.

It has been found that only by employing alcohols having a particular number of carbon atoms and various essential amounts of said alcohol, propylene oxide, and mixtures of ethylene oxide and propylene oxide can products be prepared which are liquid, low-foaming, have superior wetting properties, and in general, possess enhanced detergency and/or scourability. Moreover, the surfactant products of the invention have cloud points in the range from about 20° C. to about 60° C., which are desirable for a wide variety of applications.

Alcohols which may be employed in the preparation of the surfactants of the present invention are those primary, straight- and branched-chain aliphatic alcohols which contain 7 to 11, and preferably 8–10, carbon atoms in the chain. Mixtures of the alcohols may also be used. Exemplary suitable alcohols are 2-ethylhexanol; n-heptanol; 2,6-dimethyl-1-heptanol; n-octanol; 3,7-dimethyl-1-octanol; n-nonanol; n-decanol; n-undecanol; 2,4,4-trimethyl-1-pentanol; 2,3-dimethyl-1-pentanol; 2-propyl-1-heptanol and mixtures thereof.

The surfactants of the present invention are prepared by condensing an alcohol or mixture of alcohols, as described herein, with propylene oxide and a mixture of ethylene oxide and propylene oxide in two distinct steps. In the first step, propylene oxide or substantially only propylene oxide is added to the alcohol and, in the second step, a mixture of ethylene oxide and propylene oxide is added to the reaction product of the first step. This procedure enables the preparation of nonionic surfactants which have a block of oxypropylene groups proximate to the alcoholic portion of the surfactant and then oxyethylene groups and oxypropylene groups randomly distributed proximate to the oxypropylene block portion of the surfactant. Adding the alkylene oxides in steps as herein described provides for the preparation of surfactants that are liquid, low-foaming, yet still possess superior wetting characteristics and generally good scouring and/or detergency properties.

The products of this invention have a block-random structure. As mentioned above, the number of carbon atoms in the alcohol chain, the amount of alkylene oxides used and the order of addition of the alkylene oxides are all very important factors. In order to obtain the surfactants of this invention it is very important that from 2 to 15 moles of propylene oxide be added to a primary alcohol having 7 to 11 carbon atoms such that the sum of the number of carbon atoms in the alcohol and the number of moles of propylene oxide added thereto be an amount of from at least 12 to about 22 and preferably to about 20, and, then, that the mixture of oxides added thereto be in a molar ratio of ethylene oxide to propylene oxide of from 1:1, and preferably from about 2:1, to about 5:1. Not only is it important that the ratio of ethylene oxide to propylene oxide in the mixture of oxides added to the block adduct be maintained within the above-stated range, but that the amount of oxides employed be such that the surfactant product contains a total molar ratio of oxyethylene groups to oxypropylene groups from 0.2:1 to about 1.5:1, and, preferably, from about 0.3:1 to about 1.4:1.

The products of the invention are generally prepared by condensing the alcohol with propylene oxide during the first step in the presence of an alkaline catalyst. Catalysts which may be employed include sodium hydroxide, potassium hydroxide, sodium acetate, trimethylamine and preferably an alkali metal alcoholate of the alcohol. Any other types of catalysts commonly used for alkylene oxide addition 'reactions' with reactive hydrogen compounds may also be employed. After the condensation reaction in the first step is completed, a mixture of ethylene oxide and propylene oxide is added to the reaction mixture from the first step, generally until a product having the desired cloud point is obtained. The condensation reaction in both the first and second steps are preferably carried out at elevated temperatures and pressures. After the condensation reaction is completed, the catalyst is removed from the reaction mixture by any known procedure such as neutralization and filtration, or ion exchange.

This invention will become more clear when considered together with the following examples which are set forth as being merely illustrative of the invention and which are not intended, in any manner, to be limitative thereof.

EXAMPLE I

Into a 2-liter, 4-necked, round-bottom flask equipped with a stirrer, thermowell, nitrogen purge, and heating mantle, 520 grams (4.0 moles) of 2-ethylhexanol was charged. The alcohol was heated to 40° C. with stirring, and the system was nitrogen-purged for 15 minutes. Flake 90 percent potassium hydroxide (8 grams—0.2 percent based on total charge) was added and the mixture was heated to 100° C. until the potassium hydroxide dissolved. A reflux-still head was added to the apparatus, the pressure was reduced to 12 mm Hg, and the mixture was heated at 100° C. for a one-hour period to remove water that was present. The reaction product was charged to a 1.5—gallon, stirred, stainless steel reactor in a nitrogen atmosphere and the reactor was then closed. A pressure of 5 psig of nitrogen was put on the reactor and the contents were heated to 100° C. The pressure in the reactor was adjusted to 10 psig and 1856 grams (32 moles) of propylene oxide were fed to the reactor at 110° C. using a laboratory recycle pump. The pressure was allowed to increase to 60 psig and the system was maintained at these pressure and temperature conditions while continuing to feed propylene oxide to the reactor. After the addition of propylene oxide was completed, about 4 hours, the system was "cooked out" at 110° C. for an additional 3 hours to insure complete reaction of the propylene oxide and was then cooled.

The reactor was then pressurized with nitrogen to 15 psig and heated to 110° C. The pressure was adjusted to 20 psig with nitrogen and a 75/25 weight percent mixture of ethylene oxide and propylene oxide was slowly fed to the reactor at 110° C. until the pressure was increased to 60 psig. The mixture of alkylene oxides was fed to the reactor at 110° C. while maintaining a pressure of 60 psig until the product was determined to have a cloud point of 20° C. When the addition of mixed oxides was completed the reaction mixture was "cooked out" at 110° C. for an additional 2 hours and then cooled.

Upon cooling, 1600 grams of the product (Sample A) were discharged from the reactor in a nitrogen atmosphere to a container containing a glacial acetic acid. The reactor was then closed, heated to 100° C., pressurized to 5 psig with nitrogen and a 75/25 weight percent mixture of ethylene oxide and propylene oxide was slowly fed to the reactor at 110° C. until the pressure was increased to 60 psig. An additional amount of the mixture of ethylene oxide/propylene oxide was fed to the reactor at 110° C. while maintaining a pressure of 60 psig until the product was determined to have a cloud point of 42° C. The reaction mixture was "cooked out" at 110° C. for an additional 2 hours and then cooled. The cooled reaction product (Sample B) was discharged from the reactor in a nitrogen atmosphere to a container containing glacial acetic acid.

Each of the reaction products of this example (Samples A and B) was neutralized to a pH of 6.5 to 6.8 with additional glacial acetic acid while maintaining a nitrogen atmosphere and stripped at 100° C. at one mm Hg for one hour to remove any unreacted alkylene oxides.

Sample A was a clear liquid determined to have a molecular weight of 897; a cloud point (ASTM D 2024-65) in a 1% water solution of 20.5° C.; a freezing point lower than −40° C.; and a surface tension at 25° C. in a 0.1% water solution of 31.3 dynes/cm at 25° C. The product was determined to have a structure wherein a block of 8.4 oxypropylene groups was proximate the alcohol moiety and 4.8 oxyethylene groups and 1.2 oxypropylene groups were randomly distributed proximate the oxypropylene block.

Sample B was a clear liquid determined to have a molecular weight of 1125; a cloud point in a 1% water solution of 42° C.; a freezing point lower than −40° C.; and a surface tension at 25° C. in a 0.1% water solution of 31.5 dynes/cm at 25° C. The product was determined to have a structure wherein a block of 8.4 oxypropylene groups was proximate the alcohol moiety and 8.7 oxyethylene groups and 2.2 oxypropylene groups were randomly distributed proximate the oxypropylene block.

Foaming, wetting, and scouring performance tests were run on the Sample A and Sample B products and the results are summarized in Table I.

It is apparent from the performance test results reported in Table I that Sample A and Sample B are liquid, nonionic surfactants which are low-foaming, and have superior wetting characteristics, particularly when used at a temperature at or near its cloud point. Moreover, such compositions exhibit generally good scouring properties.

TABLE I

|  | Sample A | Sample B |
|---|---|---|
| Carbon Atoms - alcohol moiety | 8 | 8 |
| Sum of carbon atoms and oxypropylene block groups | 16.5 | 16.5 |
| Total molar ratio EO/PO | .50 | .82 |
| Cloud point | 20.5° C. | 42° C. |
| Ross-Miles Foam Test (ASTM-D 1173-53) 0.2% Surfactant distilled water | | |
| 50° C. Initial Foam Height (mm) | 14 | 75 |
| Final (mm) | 4 | 16 |
| 25° C. Initial (mm) | 20 | 111 |
| Final (mm) | 6 | 16 |
| Draves Wetting (AATCC, Method 17-1977) | | |
| 20-second wetting concentration 25° C. | 0.057% | 0.069% |
| 40° C. | — | 0.043% |
| Scouring Tests Test fabrics soil cloth, unfinished Terg-o-tometer, 0.1% surfactant conc. 150 ppm water Hardness, 50° C. | | |
| 100% Cotton   % Soil Removal | 14 | 29 |
| % Redeposition Index | 83 | 94 |
| Polyester/Cotton   % Soil Removal | 21* | 39* |
| % Redeposition Index | 77 | 99 |

*Soil removal for water without surfactant averages about 6%

EXAMPLE II

Using the apparatus and procedure of Example I, a nonionic surfactant was prepared from an initial charge of 1040 grams (8.0 moles) of octanol to which was added 3712 grams (64 moles) of propylene oxide during the first stage of the process and then a sufficient amount of a 75/25 weight percent mixture of ethylene oxide and propylene oxide to prepare a product with a cloud point of 21° C.

A clear, colorless, liquid product was obtained which was determined to have a molecular weight of 816; a cloud point of 21° C.; a freezing point lower than −40° C.; a viscosity of 70.8 centistokes at 25° C.; and a surface tension at 25° C. in a 0.1% water solution of 31.4 degrees/cm. The structure of the product was determined to have a block of 8.0 oxypropylene groups proximate the alcohol moiety and 3.8 oxyethylene groups and 0.95 oxypropylene groups randomly distributed proximate the oxypropylene block.

Using the procedures described in Example I, foaming, wetting, and scouring performance tests were run and the results determined in Table II, below.

TABLE II

| Ross-Miles Foam Test | |
|---|---|
| 50° C. Initial Foam Height (mm) | 13 |
| Final (mm) | 3 |
| 25° C. Initial (mm) | 24 |
| Final (mm) | 6 |
| Drave's Wetting at 25° C. | |
| 20-Second Wetting Concentration | 0.037% |
| Scouring Cotton at 50° C. | |
| Soil Removal | 30% |
| Redeposition Index | 95% |

EXAMPLE III

Using the procedure and apparatus of Example I, a series of products was prepared using 2-ethylhexanol as the starting alcohol and, for comparison, starting alcohols containing 6 carbon atoms (2-methylpentanol) and 12 carbon atoms (dodecanol). The following proportion of ingredients was used:

| Product | Alcohol | Propylene Oxide (moles) | EO/PO Mixture (weight percent) |
|---|---|---|---|
| A | 2 ethylhexanol 395 grams (3.0 moles) | 1044 grams (18 moles) | 65/35 |
| B | 2 ethylhexanol 395 grams (3.0 moles) | 1044 grams (18 moles) | 65/35 |
| C | dodecanol 930 grams (5.0 moles) | 580 grams (10 moles) | 60/40 |
| D | dodecanol 930 grams (5.0 moles) | 580 grams (10 moles) | 60/40 |
| E | 2-methylpentanol 357 grams (3.5 moles) | 2233 grams (38.5 moles) | 80/20 |
| F | 2-methylpentanol 357 grams (3.5 moles) | 2233 grams (38.5 moles) | 85/15 |

Properties of each of the products of this Example are summarized in Table III and performance test results for each of the products are summarized in Table IV. Each of the products of this example were clear, colorless liquids.

Product A had a structure wherein a block of 5.9 oxypropylene groups was proximate the alcohol moiety and 4.3 oxyethylene—1.8 oxypropylene groups were randomly distributed proximate the oxypropylene block. The total EO/PO molar ratio in the product was 0.56 and the sum of carbon atoms in the alcohol moiety and block oxypropylene groups was 14.

Product B had a oxypropylene block structure similar to Product A with 7.1 oxyethylene—2.9 oxypropylene groups randomly distributed proximate the oxypropylene block. The total EO/PO molar ratio in the product and general good scouring properties particularly when used at the cloud point temperatures of the surfactant while Products C, D, E, and F were liquid, low-foaming nonionic surfactants with significantly less desirable wetting and/or scouring characteristics, particularly at temperatures at or near the cloud point of the surfactant.

TABLE III

| Product | Molecular Weight | Cloud Point | Freezer Point | Viscosity at 25° C. | Surface Tension at 25° C., 0.1% Soln. |
|---|---|---|---|---|---|
| A | 766 | 20° C. | <−40° C. | 68.2 cks | 31.2 dynes/cm |
| B | 952 | 39° C. | <−40° C. | 93.5 cks | 31.5 dynes/cm |
| C | 549 | 19° C. | <−30° C. | 42.0 cks | 30.3 dynes/cm |
| D | 722 | 38° C. | <−40° C. | 61.7 cks | 31.4 dynes/cm |
| E | 1067 | 18° C. | <−30° C. | 114.3 cks | 34.5 dynes/cm |
| F | 1238 | 39° C. | <−25° C. | 145.6 cks | 36.4 dynes/cm |

TABLE IV

|  | Product A | Product B | Product C | Product D | Product E | Product F |
|---|---|---|---|---|---|---|
| Carbon atoms in alcohol moiety | 8 | 8 | 12 | 12 | 6 | 6 |
| Cloud point | 20° C. | 39° C. | 19° C. | 38° C. | 18° C. | 39° C. |
| Ross-Miles Foam Test |  |  |  |  |  |  |
| 0.2% Surfactant in distilled water |  |  |  |  |  |  |
| 50° C. Initial Foam Height (mm) | 10 | 30 | 4 | 33 | 21 | 56 |
| Final (mm) | 0 | 7 | 1 | 6 | 5 | 8 |
| 25° C. Initial Foam Height (mm) | 15 | 85 | 88 | 117 | 13 | 34 |
| Final (mm) | 3 | 10 | 7 | 16 | 0 | 5 |
| Draves Wetting |  |  |  |  |  |  |
| 20-Second wetting concentration |  |  |  |  |  |  |
| 25° C. | 0.058 | 0.070 | 0.068 | 0.044 | 0.064 | 0.207 |
| 40° C. | — | 0.047 | — | 0.079 | — | 0.054 |
| Scouring (50° C.) |  |  |  |  |  |  |
| 100% cotton, % soil removal | 14 | 22 | — | — | — | — |
| % Redeposition Index | 83 | 77 | — | — | — | — |
| Polyester/cotton, % soil removal | 15 | 27 | 7 | 33 | 4 | 26 |
| % redeposition index | 76 | 79 | 61 | 91 | 60 | 90 | was 0.81 and the sum of carbon atoms in the alcohol moiety and block oxypropylene groups was 14.

Product C had a structure wherein a block of 2.0 oxypropylene groups was proximate the alcohol moiety and 3.3 oxyethylene—1.1 oxypropylene groups were randomly distributed proximate the oxypropylene block. The total EO/PO molar ratio in the product was 1.06 and the sum of carbon atoms in the alcohol moiety and oxypropylene block groups was 14.

Product D had a oxypropylene block structure similar to Product C with 5.7 oxyethylene—1.8 oxypropylene groups randomly distributed proximate the oxypropylene block. The total EO/PO molar ratio in the product was 1.49 and the sum of carbon atoms and oxypropylene block groups was 14.

Product E had a structure wherein a block of 10.8 oxypropylene groups was proximate the alcohol moiety and 6.1 oxyethylene—1.2 oxypropylene groups were randomly distributed proximate the oxypropylene block. The total EO/PO molar ratio in the product was 0.57 and the sum of carbon atoms in the alcohol moiety and oxypropylene block groups was 17.

Product F had a oxypropylene block structure similar to Product E with 9.4 oxyethylene—1.6 oxypropylene groups randomly distributed proximate the oxypropylene block. The total EO/PO molar ratio in the product was 0.76 and the sum of carbon atoms in the alcohol moiety and oxypropylene block groups was 17.

It is apparent from the results reported in Table IV that Products A and B were liquid, low-foaming nonionic surfactants with superior wetting characteristics

What is claimed is:

1. A liquid, low-foaming nonionic surfactant composition having a block-random structure represented by the formula:

$$R\text{-}O\text{-}A_x\text{-}B\text{-}H$$

wherein R is a primary alkyl group having from 7 to 11 carbon atoms; A is oxypropylene groups; x is an integer of from 2 to about 15 such that the sum of carbon atoms in said alkyl group and x is from 12 to about 22; and B is a random mixture of oxyethylene and oxypropylene groups the molar ratio of oxyethylene to oxypropylene being from 1:1 to about 5:1 such that the total molar ratio of oxyethylene to oxypropylene in A and B is from 0.2:1 to 1.5:1, said composition having a cloud point of about 20° to about 60° C.

2. The liquid, nonionic surfaction of claim 1 wherein R is a straight- or branched-chain alkyl group having from 8 to 10 carbon atoms.

3. The liquid, nonionic surfactant of claim 1 wherein the molar ratio of oxyethylene to oxypropylene in the random mixture is from about 2:1.

4. The liquid, nonionic surfactant of claim 1 wherein R is the residue of 2-ethylhexanol.

5. The liquid, nonionic surfactant of claim 1 wherein x is an integer up to about 12.

6. The liquid, nonionic surfactant of claim 1 wherein the sum of the number of carbon atoms in R and x is a value up to about 20.

* * * * *